US00PP14565P29

(12) United States Plant Patent
Harbaugh et al.

(10) Patent No.: US PP14,565 P2
(45) Date of Patent: Feb. 24, 2004

(54) CALADIUM PLANT NAMED 'FLORIDA MOONLIGHT'

(50) Latin Name: *Caladium×hortulanum*
Varietal Denomination: Florida Moonlight

(75) Inventors: Brent K. Harbaugh, Bradenton, FL (US); Baldwin D. Miranda, Naples, FL (US)

(73) Assignee: Florida Foundation Seed Producers Inc., Greenwood, FL (US)

( * ) Notice: Subject to any disclaimer, the term of this patent is extended or adjusted under 35 U.S.C. 154(b) by 0 days.

(21) Appl. No.: 10/378,464

(22) Filed: Mar. 4, 2003

(51) Int. Cl.[7] ..... A01H 5/00
(52) U.S. Cl. ..... Plt./263
(58) Field of Search ..... Plt./373

*Primary Examiner*—Bruce R. Campell
*Assistant Examiner*—A. Para

(57) ABSTRACT

A distinct cultivar of Caladium plant named 'Florida Moonlight', characterized by its large heart shaped leaves, white interveinal leaf surfaces, and white primary veins; demonstrated potential to produce a superior number of leaves that emerge sooner than other white cultivars when tubers are forced in pots; and superior vigor when grown in outdoor landscapes.

2 Drawing Sheets

Figure 1:
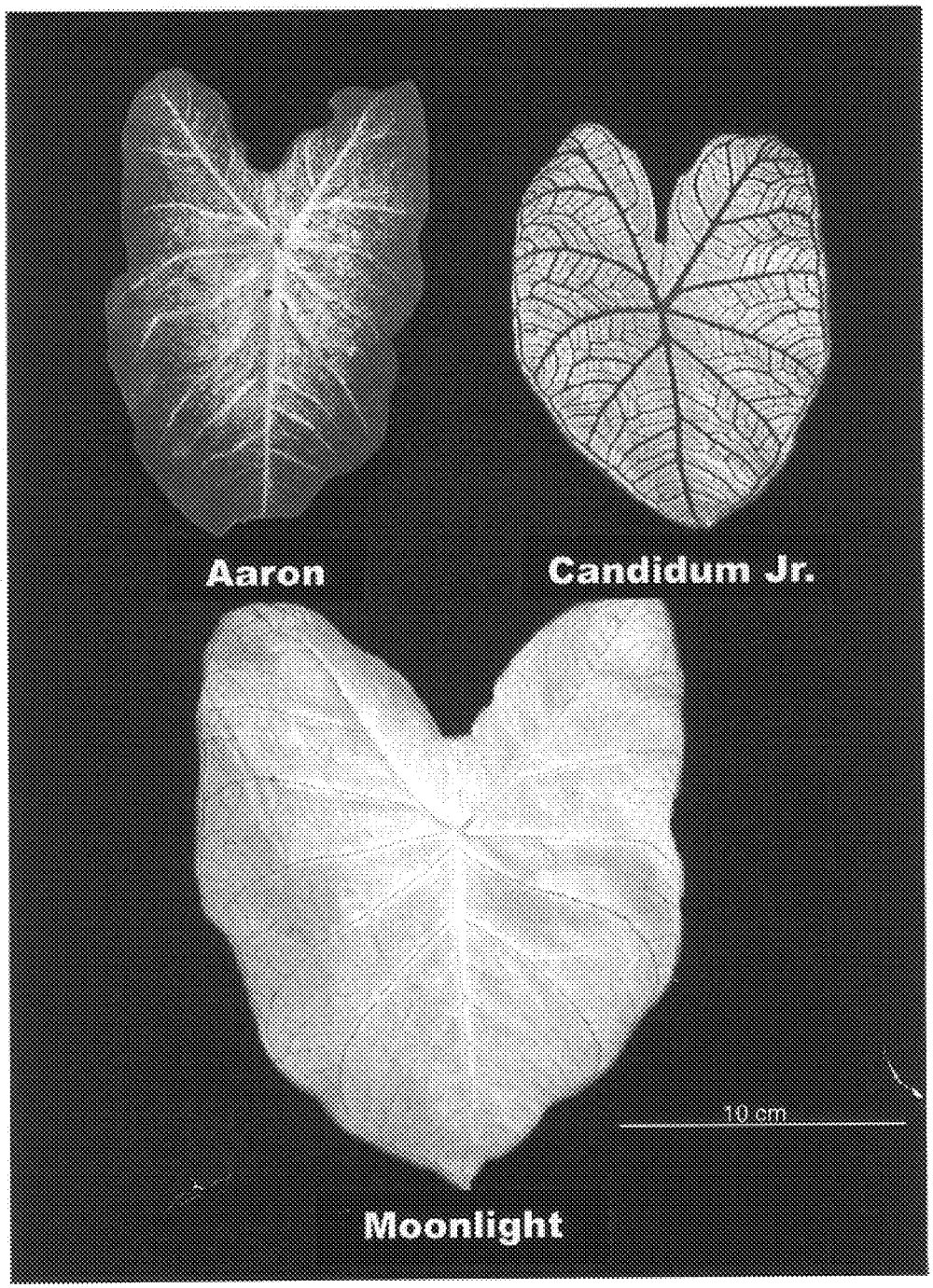

Botanical classification: *Caladium×hortulanum.*
Variety denomination: 'Florida Moonlight'.

BACKGROUND OF THE INVENTION

'Florida Moonlight' was a seedling initially evaluated in 1985 as GC85-245 originating from the cross-pollination of the *Caladium×hortulanum* cultivar Aaron with the cultivar Candidum Junior made in 1982 in a greenhouse in Bradenton, Fla. 'Aaron', not patented, was selected as the female (seed parent) parent because of its vigor, tuber yield, white-veined character, and excellent sun tolerance. 'Candidum Junior', not patented, was the male (pollen) parent selected because of its leaf production, multi-segmented tubers, bright white interveinal leaf surfaces, and quality as a container plant. Ancestry of 'Aaron' is unknown but 'Candidum Junior' is believed to be a field mutation of 'Candidum'. Asexual propagation of tubers and evaluation in field and pot studies since 1985 have shown that the unique features of this new Caladium plant are stable and reproduced true to type in successive generations of asexual propagation.

SUMMARY OF THE INVENTION

The new Caladium has not been observed under all possible environmental conditions. The phenotype may vary somewhat with variations in the environment such as light intensity and temperature, without, however, any variance in genotype.

Caladiums are utilized in the ornamental industry as potted plants and landscape plants. They have a diversity of leaf colors that arise from red, pink, and white pigments displayed in solid, spot, and/or blotch patterns in interveinal areas. Veins and leaf margins may be colored or green adding to the diversity of patterns. For plants to be successful in the landscape, they must be vigorous, brightly colored, and have large leaves (unless used for border plants such as is the case for strap or lance leaved cultivars). When forced in containers to be used as an ornamental potted plant, shorter plants with many leaves that emerge quickly are desirable traits. The new caladium plant, 'Florida Moonlight', has distinct solid white interveinal leaf surfaces on heart shaped leaves, white primary veins, and a very narrow green margin. It is different in color (FIG. 1) from 'Aaron', the female parent, which has a wide green margin and the white interveinal pattern is unstable from leaf to leaf. That is, leaves on one plant of 'Aaron' may range in color from only white veins to nearly ¾ the interveinal area of the leaf having a solid white center. It is different in color (FIG. 1) from 'Candidum Junior', the male parent, which has green primary veins resulting in a netted pattern. 'Florida Moonlight' has performed well in landscape settings in a number of trials showing the vigor necessary for landscape use. In addition, the new cultivar produces many leaves when the terminal is excised and tubers forced in pots, making it suitable for both a potted plant and a landscape plant. Tuber production, a necessary consideration for commercialization of a cultivar by the caladium tuber producing industry, has been excellent with tubers produced in the ideal sizes as described in the description section.

BRIEF DESCRIPTION OF THE PHOTOGRAPHS

The accompanying colored photographs illustrates the overall appearance of the new cultivar, showing the colors as true as it is reasonably possible to obtain in colored reproductions of this type. Colors in the photograph may differ slightly from the color values cited in the detailed botanical description, which accurately describe the colors of the new Caladium.

The first photograph, labeled FIG. 1, illustrates typical color patterns of leaf blades of 'Aaron' (female parent) and 'Candidum Junior' (male parent) in comparison with the new Caladium plant 'Florida Moonlight'.

Figure 2:
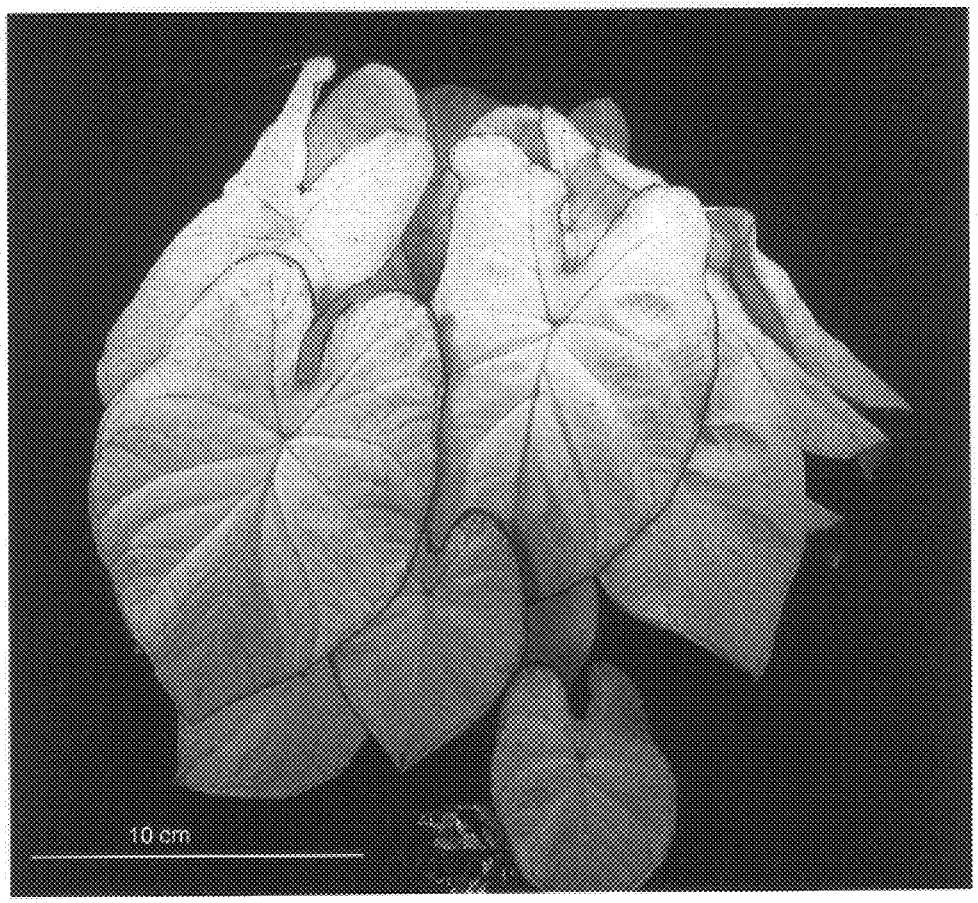

The second photograph, labeled FIG. 2, illustrates the overall appearance of the new cultivar, Florida Moonlight. The photograph is a side perspective view of a typical plant of 'Florida Moonlight' grown in a container.

DETAILED BOTANICAL DESCRIPTION

The following is a detailed description of the new variety with color terminology in accordance with British Color Council and The Royal Horticultural Society, Horticultural Colour Chart, except where general color terns of ordinary dictionary significance are obvious. Wherein dimensions, sizes, and other characteristics are given, it is to be understood that such characteristics are approximations of averages set forth as accurately as practicable. The description herein is from specimens sixty days old grown in Bradenton, Fla., in 1996–2001. Plants used for describing color were grown in 15 cm containers in a 40% shaded greenhouse from No. 1 (3.8<6.4 cm diameter) de-eyed tubers.

Botanical classification: *Caladium×hortulanum* cultivar Florida Moonlight.

Propagation:

*Type.*—By tuber division.

*Time to develop roots and sprout.*—51 days (Spring—15° C. night to 29° C. day). 27 days (Summer — 21° C. night to 35° C. day).

*Root description.*—Dense, thick roots (up to 3 mm at the basal end) with little branching and few lateral roots.

Plant description:

*Plant shape.*—Upright, symmetrical.

*Plant height.*—About 59 cm from top of soil to top of leaf plane 7 months from planting tubers in ground beds in full sun.

*Leaf blade.*—Leaves are peltate, sagitate-cordate, 25–29 cm long and 19–21 cm wide, with green (RHS 129D) palmate-pinnate venation. The upper surface has a green (RHS 131A) margin, 1 mm wide, bordering the entire leaf except for the basal leaf valley where it is grayed-purple (RHS 185A). Interveinal areas are white (RHS 155C). Netted green (RHS 131A) venation occurs on 50–75% of leaf surface. The undersurface has a grayed-green (RHS 191A) margin, 1 mm wide. Primary veins are grayed-green (RHS 194B) and netted venation, grayed-green (RHS 191A), occurs on 50–75% of leaf surface. Interveinal areas are white (RHS 155B).

*Petiole.*—Petioles are 4–8 mm in diameter, with grayed-orange (RHS 177D) base color densely speckled with brown (RHS 200A).

*Tuber.*—Tubers are multi-segmented; a tuber 6.4–8.9 cm in diameter will typically bear 5–7 dominant buds. Tuber surfaces are brown (RHS 200B) with the cortical area yellow (RHS 13C).

*Inflorescence.*—The flowering and reproductive organs do not differ in character from other caladium plants.

Performance

'Florida Moonlight' was evaluated for tuber production in side-side comparisons with other cultivars at the Gulf Coast REC Bradenton, Fla. during 1998, 1999, and 2000. The soil was EauGallie fine sand with about 1% organic matter and a pH of 6.2. Plants were grown in a plastic-mulched raised-bed system maintaining a constant water table with seep irrigation. Ground beds were fumigated 3 weeks before planting with a mixture of 67% methyl bromide and 33% chloropicrin (by volume) at 392 kg•ha$^{-1}$. The beds were 91 cm wide and 20 cm high with 2.54 cm caladium seed pieces planted 15 cm apart in 3 rows spaced 15 cm apart. A 18N-2.6P-10K 8–9 month controlled release fertilizer was applied to the bed surface at time of fumigation with N at 336 kg•ha$^{-1}$. Plots were organized in a randomized complete block design consisting of three replications. An analysis of variance combined over years was conducted in order to compare the performance of 'Florida Moonlight' to 'June Bride' and other commercially important white fancy-leaf cultivars.

Marketable tuber yields of 'Florida Moonlight' exceeded those of 'June Bride' but were similar to 'Candidum' and 'Candidum Junior' (Table 1). Sixty-five percent of 'Florida Moonlight' tubers were in the No.1 and No. 2 grades, heavily used by container plant producers, compared to 48% for 'June Bride'. 'Candidum Junior', a popular variety with container plant growers, produced a similar number of marketable tubers as 'Florida Moonlight' but fewer jumbo and No. 1 tubers resulting in a lower estimate of economic value based on the production index (Table 2). Although 'Florida Moonlight' had less marketable tuber weight than 'June Bride' or 'Candidum', its ability to produce a greater number of tubers, albeit smaller, resulted in a similar production index.

Landscape performance of cultivars was compared in side-side comparisons of plants grown under full-sun conditions in 1996, 1998, and 1999 (Table 3) on the same plots used for evaluating tuber production. Plant height, number of leaves, and foliar characteristics were recorded approximately 7 months after planting. 'Florida Moonlight' displayed more landscape vigor than 'June bride' by producing taller plants with a greater number of leaves. Leaf size of 'Florida Moonlight' and 'June bride' was similar though slightly narrower for 'June bride'.

'Florida Moonlight' tubers were forced in 10-cm containers and side-side comparisons of growth were made with three white-fancy commercial cultivars in 2001. The root medium contained 3 sedge peat/: 1½ coarse horticultural vermiculite: 1 sand (by volume) amended with (in kg•m$^{-3}$) 3 dolomitic lime, 3 calcitic lime, 3 single superphosphate, 0.6 micro nutrient mixture and 1.8 14N-6.1P-11.6K 3–4 month controlled release fertilizer. The study was conducted in a glasshouse with 40% light exclusion during the summer in Bradenton, Fla. Average daily temperatures were approximately 15° C. night and 29° C. day during the experiment. Plant height, number of leaves, and foliar characteristics were recorded 3 weeks after plants reached the marketable stage.

'Florida Moonlight' was much quicker in producing a marketable container plant than 'June Bride' from either intact or de-eyed tubers and similar to 'Candidum' and 'Candidum Junior' (Table 4). Leaf production also was superior for 'Florida Moonlight' compared with 'June Bride' from either intact or de-eyed tubers.

Excision of dominant buds of 'Florida Moonlight' resulted in a reduction in plant height, leaf length and leaf width while increasing number of leaves. Visual quality was rated when plants reached the marketable stage. The subjective rating was based on the ratio of plant height to container height, fullness of plant form, and attractiveness. The performance of 'Florida Moonlight' from intact tubers suggested that it might be unsuitable for 10-cm containers without de-eyeing because of plant height. When tubers were de-eyed, 'Florida Moonlight' produced an excellent plant with visual quality superior to 'June bride' and 'Candidum'.

TABLE 1

Tuber grade distribution of caladium cultivars harvested in 1998, 1999 and 2000, Bradenton, Fla. Values represent the means of three replications of 30 propagules per 1.2 $m^2$ plot per year, averaged over 3 years.

| | Marketable tubers by grade[z] (%) | | | | | |
|---|---|---|---|---|---|---|
| Cultivar | Super Mammoth | Mammoth | Jumbo | No. 1 | No. 2 | Marketable Tubers (no.) |
| Candidum | 2 | 18 | 27 | 28 | 24 | 41 |
| Candidum Jr. | 0 | 9 | 20 | 38 | 33 | 44 |
| June Bride | 1 | 14 | 36 | 31 | 17 | 38 |
| Florida Moonlight | 0 | 8 | 27 | 48 | 17 | 45 |
| LSD ($\alpha$ = 0.05) | 2 | 5 | 6 | 6 | 6 | 5 |

[z]Tubers graded by maximum diameter; super mammoth (≧11.4 cm); mammoth (≧8.9 < 11.4 cm); jumbo (≧6.4 < 8.9 cm); No.1 (≧3.8 < 6.4 cm); No.2 (≧2.5 <3.8).

TABLE 2

Tuber weights and the production index for caladium cultivars harvested in 1998, 1999 and 2000, Bradenton, Fla. Values represent the means of three replications with 30 propagules per 1.2 $m^2$plot per year, averaged over 3 years.

| | Tuber wt (g) | | | | Production |
|---|---|---|---|---|---|
| Cultivar | Marketable | Seed | Total | Mean | index |
| Candidum | 4728 | 227 | 4954 | 119 | 125 |
| Candidum Jr. | 3427 | 371 | 3798 | 80 | 107 |
| June Bride | 4691 | 129 | 4820 | 123 | 120 |
| Florida Moonlight | 3600 | 124 | 3723 | 82 | 120 |
| LSD ($\alpha$ = 0.05) | 606 | 66 | 600 | 15 | 13 |

[z]Mean = marketable weight/marketable number.
[y]The production index is an indicator of the economic value of the crop calculated as: N (no. 2's) + 2N (no. 1's) + 4N (jumbo) + 6N (mammoth)+ 6N (super mammoth); where N = number of tubers in each grade.

TABLE 3

Plant performance after 7 months for caladium cultivars grown in full sun from 2.5 cm tubers in 1996, 1998 and 1999, Bradenton, Fla. Values presented are means of three replications with three plants measured per plot per year, averaged over 3 years.

| | Plant height | | Leaf | |
|---|---|---|---|---|
| | (cm) | Leaves | Length | Width |
| Candidum | 78 | 15 | 31 | 21 |
| Candidum Jr. | 64 | 14 | 28 | 19 |
| Florida Moonlight | 73 | 18 | 27 | 19 |
| June Bride | 59 | 9 | 27 | 17 |
| LSD ($\alpha$ = 0.05) | 6 | 4 | 2 | 2 |

TABLE 4

Plant performance for caladium cultivars grown from intact (I) or de-eyed (D) No. 1 tubers (>3.8 < 6.4 cm diameter) in 10 cm containers in a 40% shaded glasshouse, 2001. Values represent the means of seven plants produced from intact or de-eyed No. 1 tubers planted individually per container.

| | Days to market[z] | | Plant ht (cm) | | Leaves Number (cm) | | Leaves Length (cm) | | Leaves Width | | Visual quality[y] | |
|---|---|---|---|---|---|---|---|---|---|---|---|---|
| | I | D | I | D | I | D | I | D | I | D | I | D |
| Candidum | 61 | 51 | 26 | 23 | 10 | 11 | 20 | 18 | 16 | 13 | 3.0 | 3.3 |
| Candidum Jr. | 54 | 53 | 26 | 20 | 12 | 15 | 22 | 16 | 15 | 12 | 3.2 | 4.0 |
| Florida Moonlight | 59 | 58 | 30 | 26 | 11 | 13 | 26 | 21 | 19 | 14 | 3.7 | 4.4 |
| June Bride | 76 | 72 | 31 | 27 | 6 | 9 | 27 | 22 | 18 | 14 | 3.0 | 3.4 |
| LSD ($\alpha$ = 0.05) | 11 | 9 | 7 | 5 | 3 | 3 | 5 | 4 | 4 | 3 | 1.0 | 0.7 |

[z]Number of days from planting to the fifth leaf unfurled.
[y]Rated on a 1–5 scale where 1 = poor and 5 = excellent.

It is claimed:

1. A new and distinct cultivar of Caladium plant named 'Florida Moonlight', as illustrated and described.

* * * * *

Florida Moonlight, a distinct cultivar of Caladium plant

Florida Moonlight, a distinct cultivar of Caladium plant